(12) United States Patent
Griffey et al.

(10) Patent No.: US 6,933,326 B1
(45) Date of Patent: Aug. 23, 2005

(54) PARTICULATE ACELLULAR TISSUE MATRIX

(75) Inventors: Edward S. Griffey, Phillipsburg, NJ (US); Stephen A. Livesey, Eltham (AU); Charles M. Schiff, The Woodlands, TX (US); Lawrence E. Boerboom, The Woodlands, TX (US)

(73) Assignee: LifeCell Coporation, The Woodlands, TX (US)

( * ) Notice: Subject to any disclaimer, the term of this patent is extended or adjusted under 35 U.S.C. 154(b) by 0 days.

(21) Appl. No.: 09/762,174

(22) PCT Filed: Jun. 18, 1999

(86) PCT No.: PCT/US99/13861

§ 371 (c)(1),
(2), (4) Date: Nov. 22, 2000

(87) PCT Pub. No.: WO99/65470

PCT Pub. Date: Dec. 23, 1999

Related U.S. Application Data
(60) Provisional application No. 60/089,865, filed on Jun. 19, 1998.

(51) Int. Cl.[7] ............................................. A61K 35/34
(52) U.S. Cl. ..................... 523/113; 424/422; 424/423; 424/426; 424/499; 514/21; 514/801; 523/309
(58) Field of Search .................................. 424/422–423, 424/426, 499; 514/21, 801; 523/113, 309

(56) References Cited

U.S. PATENT DOCUMENTS

| | | | |
|---|---|---|---|
| 4,347,841 A | | 9/1982 | Benyo et al. |
| 4,350,629 A | | 9/1982 | Yannas et al. |
| 4,352,883 A | | 10/1982 | Lim |
| 4,582,640 A | | 4/1986 | Smestad et al. .......... 260/123.7 |
| 4,776,173 A | * | 10/1988 | Kamarei et al. ................ 62/63 |
| 4,902,508 A | | 2/1990 | Badylak et al. ................ 424/95 |
| 4,969,912 A | | 11/1990 | Kelman et al. ................ 623/66 |
| 5,104,957 A | | 4/1992 | Kelman et al. ............. 527/201 |
| 5,131,850 A | | 7/1992 | Brockbank ...................... 435/1 |
| 5,160,313 A | | 11/1992 | Carpenter et al. ............. 600/36 |
| 5,256,140 A | * | 10/1993 | Fallick ......................... 424/572 |
| 5,275,826 A | * | 1/1994 | Badylak et al. .............. 424/551 |
| 5,332,802 A | | 7/1994 | Kelman et al. ............. 530/356 |
| 5,332,804 A | | 7/1994 | Florkiewicz et al. ........ 530/399 |
| 5,489,304 A | | 2/1996 | Orgill et al. ................... 623/15 |
| 5,613,982 A | | 3/1997 | Goldstein ..................... 623/11 |
| 5,632,778 A | | 5/1997 | Goldstein ..................... 623/11 |
| 5,648,330 A | | 7/1997 | Pierschbacher et al. ....... 514/11 |
| 5,695,998 A | * | 12/1997 | Badylak et al. .............. 435/391 |
| 5,712,252 A | | 1/1998 | Smith ........................... 514/21 |
| 5,728,752 A | | 3/1998 | Scopelianos et al. ........ 523/113 |
| 5,739,176 A | | 4/1998 | Dunn et al. .................. 523/113 |
| 5,800,537 A | * | 9/1998 | Bell ......................... 424/195.1 |
| 5,893,888 A | | 4/1999 | Bell |
| 6,027,743 A | * | 2/2000 | Khouri et al. ............... 424/423 |
| 6,096,347 A | * | 8/2000 | Geddes et al. ............... 424/551 |

FOREIGN PATENT DOCUMENTS

| | | | |
|---|---|---|---|
| CA | 1336812 | 2/1989 | .......... A61K/38/39 |
| CA | 1336812 | 8/1995 | .......... A61K/38/39 |
| FR | 1552286 | 2/1967 | |
| FR | 2104349 | 4/1972 | |
| FR | 2236539 | 7/1975 | |
| WO | WO84/04880 | 12/1984 | |
| WO | WO93/05665 | 4/1993 | ............. A23L/1/18 |
| WO | WO93/05665 | 6/1993 | ............ C12N/5/00 |
| WO | WO 99/65470 | 12/1999 | |

OTHER PUBLICATIONS

Brendel et al. (1980) "Vascular Basement Membranes: Preparation and Properties of Material Isolated with the use of Detergents" *The Cerebral Microvasculature* eds. Eisenberg and Suddith.

Duhamel et al. (1981) "Morphology of Bovine Cerebral and Retinal Microvascular Basement Membranes and Electrophoretic Characterization of Differential Extracts", 11th Europe Conf. Microcirculation, Garmisch–Partenkirchen, Bibliotheca Anatomica, No. 20, pp. 134–137.

Johnson et al., (1982) "Preparation of Cell–Free Extracellular Matrix from Human Peripheral Nerve", Muscle &Nerve 5:335–344.

(Continued)

*Primary Examiner*—Peter Szekely
(74) *Attorney, Agent, or Firm*—Fish & Richardson P.C.

(57) ABSTRACT

A method of processing an acellular tissue matrix to give a particulate acellular tissue matrix includes: cutting sheets of dry acellular tissue matrix into strips; cryofracturing the dry acellular tissue matrix strips at cryogenic temperatures; separating the resulting particles by size at cryogenic temperatures; and freeze drying the fraction of particles desired size to remove any moisture that may have been absorbed to give a dry particulate acellular tissue matrix. Rehydration of the dry particulate acellular tissue matrix may take place just prior to use. The particulate acellular tissue may be applied to a recipient site, by way of injection, spraying, layering, packing, in-casing or combinations thereof. The particulate acellular tissue may further include growth and stimulating agents selected from epidermal growth factor, fibroblast growth factor, nerve growth factor, keratinocyte growth factor, platelet derived growth factor, vasoactive intestinal peptide, stem cell factor, bone morphogetic proteins, chondrocyte growth factor and combinations thereof. Other pharmaceutically active compounds may be combined with the rehydrated particulate material including: analgesic drugs; hemostatic drugs; antibiotic drugs; local anesthetics and the like to enhance the acceptance of the implanted particulate material. The particulate material product may also be combined with stem cells selected from mesenchymal stem cells, epidermal stem cells, cartilage stem cells, hematopoietic stem cells and combinations thereof.

21 Claims, 2 Drawing Sheets

OTHER PUBLICATIONS

Ohno et al., (1980) "Human placental chorionic villar extracellular matrix. 2. Solubilization and characterization from villar fragments fractionated according to their size", Biological Res. In Pregnancy, 1(2):79–89.

Reichert–Jung Cryofract® 190 Cryoblock "A complete line for Freezing and Fracturing" Brochure.

"*Freeze–Thaw Damage of Saccharomyces–Cerevisiae in Aqueous Cell Suspensions*," by K. Hayakawa, Hakkokogaku Kaishi 63 (1), 1985, 17–22.

Hayakawa, K., Freeze–Thaw Damage of Saccharomyces–Cerevisiae in Aqueous Cell Suspensions, *Hakkokogaku Kaishi*, vol. 63, No. 1, pp. 17–22.

Ohno et al., (1980) "Human placental chorionic villar extracellular matrix. 1. Preparation and chemical composition from villar fragments fractionated according to their size", Int. J. Biol. Res. In. Pregnancy, 1(1): 38–47.

\* cited by examiner

PARTICULATE ACELLULAR TISSUE MATRIX

The present invention claims priority of U.S. Provisional Patent Application No. 60/089,865; filed 19 Jun. 1998.

BACKGROUND OF THE INVENTION

Human, animal and synthetic materials are currently used in medical procedures to augment tissue or repair or correct tissue defects. To be optimum, such materials should not migrate and should promote the regeneration of normal tissue, repopulating with the host's cells, revascularizing, and integrating with the patient's own tissue without triggering an inflammatory response that results in the degradation or resorption of the material. Additionally, the manner of delivery of such material, e.g. by surgical procedure or by injection, may significantly affect the clinical applications of the material, the ease of use by the physician and the cost of the procedure.

Injectable collagen and other materials have been used clinically for a wide variety of pathological and cosmetic applications in the fields of reconstructive surgery, dermatology, oncology, otolaryngology and urology. Currently, the most widely used form of injectable collagen is derived from crosslinked bovine Type I collagen. In human clinical applications the effect of this xenogenic transplant is resorption by the human host. Patients receiving these xenogenic grafts are susceptible to an immune response to the animal collagen, requiring prescreening for existing antibodies. Examples of such materials may be found in U.S. Pat. Nos. 4,582,640; 5,104,957; 5,728,752; and 5,739,176.

Human collagen that may be injected is currently available and sold under the tradenames Autologen® and Dermologen® and is manufactured by Collagenesis. This material it typically derived from autologous collagen obtained during elective surgery or allogenic collagen from cadavers. The starting material is dissociated by mechanical means and chemically treated to remove all noncollagenous proteins. The collagen is treated with additional chemicals to mask or crosslink the adverse effects of these damaged and exposed collagen fibers. More information with regard to this technology may be found in U.S. Pat. Nos. 4,969,912 and 5,332,802.

AlloDerm®, produced by LifeCell Corporation, is an acellular tissue matrix which is produced from normal human skin using processing techniques established to remove the epidermis and cells within the dermis without significantly altering the normal biochemistry and molecular architecture of the connective tissue matrix. The resulting product is in a freeze-dried form allowing extended shelf life and ease of shipping without degradation or loss of the normal tissue matrix components. AlloDerm® is used clinically to repair or replace damaged or inadequate tissues. Reported applications for AlloDerm® include: full thickness burn injury, replacement of lost gingiva due to periodontal disease, reconstructive surgical applications involving the replacement of lost tissue or restoration of normal surface contours of skin damaged due to injury or aging neurosurgical application to replace lost dura and in urological applications such as bladder slings and pelvic floor reconstruction. AlloDerm® has been reported to integrate at the graft site where it is rapidly repopulated with the normal milieu of host cells. A reported benefit of AlloDerm® is that it maintains the structure and biochemistry of the tissue matrix, promoting normal tissue regeneration. Studies have indicated that AlloDerm® retains decorin, hyaluronic acid, chondroitin sulfates, nidogen, growth factors and other biochemical proteins present in normal soft tissues. Additionally, AlloDerm® is reported to contain the basement membranes of vascular channels and the orientation of elastin and collagen fibers of the starting dermal tissue. For these reasons it is believed that the structure and biochemistry of the AlloDerm® matrix promotes tissue regeneration. Reducing sheet AlloDerm® to a particulate suitable for injection should extend the beneficial properties of AlloDerm® to several new applications.

Methods presently used to produce currently available injectable collagen materials include mechanical disruption of the starting material in its wet, hydrated state. However, when such processes are carried out on intact autograft, allograft or xenograft tissue, damage to the matrix occurs such that following transplantation a foreign body response and rapid resorption of the tissue matrix occurs. Further, microscopic and histological analysis of material processed in such a manner exhibit mechanical disruption of the collagen fibers. Mechanical disruption of dried human or animal tissue at non-cryogenic temperatures is believed to create a similar disruption of the collagen fibers, resulting in a foreign body response by the recipient and resorption of the material.

Thus there exists an unmet need for a method of making an intact particulate acellular tissue matrix from acellular tissues.

SUMMARY OF THE INVENTION

The present invention is generally directed to a method of processing an acellular tissue matrix to give a particulate acellular tissue matrix. A general embodiment of the method of the present invention includes the steps of: cryofracturing the dry acellular tissue matrix strips at cryogenic temperatures; and separating the resulting particles by size at cryogenic temperatures. In a prefered embodiment, the method of the present invention includes: cutting sheets of dry acellular tissue matrix into strips; cryofracturing the dry acellular tissue matrix strips at cryogenic temperatures; separating the resulting particles by size at cryogenic temperatures; and freeze drying the fraction of particles desired size to remove any moisture that may have been absorbed to give a dry particulate acellular tissue matrix. Rehydration of the dry particulate acellular tissue matrix may take place just prior to use.

It is generally preferred that the cryofracturing be carried out at temperatures below 0° C. and preferably the temperature should be below about −50° C. and more preferably should be below about −100° C. Commercially available refrigerants can be used to achieve such temperatures, which may include halocarbon refrigerants, liquid carbon dioxide, liquid nitrogen, liquid argon, liquid helium and other similar such well known non-chemically reactive and thus inert and non-toxic refrigerants. The separation of the resulting particles should also be carried out at cryogenic temperatures utilizing a series of metal mesh screens suitably sized for the particle range desired. In one preferred embodiment the screens are selected so as to isolate particles having a size of about 1 micron to about 900 microns and preferably screens are selected to isolate particles having a size from about 30 microns to about 800 microns. The present invention also encompasses the product of the above described processes.

These and other features of the present invention are more fully set forth in the following description of illustrative embodiments of the invention.

BRIEF DESCRIPTION OF THE DRAWINGS

The description is presented with reference to the accompanying drawings in which.

DESCRIPTION OF ILLUSTRATIVE EMBODIMENTS

Acellular tissue matrix tissue is the result of a multistep process in which the tissue is collected from a donor and processed so as to isolate the natural tissue matrix. In its preferred form, the process includes the steps of processing biological tissues including treatment with a stabilizing solution to reduce procurement damage, treatment with a processing solution to remove cells and other antigenic tissue components, treatment with a cryoprotectant solution, freezing and storage under specific conditions to avoid functionally significant damaging ice crystal formation, drying under conditions to prevent damaging ice recrystallization, storage in the dry state at above freezing temperatures, rehydration under specific conditions and with a rehydration solution to minimize surface tension damage and further augment the selective preservation of the matrix, and reconstitution with viable cells that will not be rejected by the host.

The above summarized process for producing acellular dermal or other tissue matrix is more fully disclosed in U.S. Pat. No. 5,336,616, the entire contents of which is incorporated herein by reference.

One of skill in the art will appreciate however that other acellular tissue matrix tissues may be used in the present invention. For example, acellular tissue matrix tissue derived from xenogenic source may be used in addition to the human derived tissue disclosed above, and other tissues such as blood vessels, heart valves, fascia and nerve connective tissue may be used to create a particulate acellular matrix within the scope of the present invention. Thus in one preferred embodiment of the present invention, the method disclosed herein utilizes acellular tissue matrix tissue, herein also referred to as AlloDerm®, which is commercially available from LifeCell Corporation, The Woodlands Texas.

The process of the present invention utilizes a chemical free and minimally disruptive technique which minimizes the damage to the collagen fibers including sheared fiber ends that result from the conventional wet or dry processes previously disclosed. The resulting particulate acellular tissue matrix can be suspended in a suitable carrying agent and thereby is made suitable for delivery through hypodermic needle injection or other modes of application including, spraying, layering, packing, in-casing or combinations of these methods. One of skill in the art should also appreciate that the particulate acellular matrix may be reconstituted into a sheet, or into a gelatinous form or other forms for use.

Generally the method of the present invention includes the steps of: cryofracturing the dry acellular tissue matrix strips at cryogenic temperatures; and separating the resulting particles by size at cryogenic temperatures. In a preferred embodiment, the method of the present invention includes: cryofracturing the dry acellular tissue matrix strips at cryogenic temperatures; separating the resulting particles by size at cryogenic temperatures; and freeze drying the fraction of particles desired size to remove any moisture that may have been absorbed to give a dry particulate acellular tissue matrix. In a more preferred embodiment the method of the present invention includes: cutting sheets of dry acellular tissue matrix into strips; cryofracturing the dry acellular tissue matrix strips at cryogenic temperatures; separating the resulting particles by size at cryogenic temperatures; freeze drying the fraction of particles desired size to remove any moisture that may have been absorbed to give a dry particulate acellular tissue matrix; and rehydrating the dry particulate acellular tissue matrix.

Preferably the dry acellular tissue matrix is cryogenically cooled to a temperature that permits the cryogenic fracturing, shattering or milling of the material. In one embodiment of the present invention a sterilized homogenizer cooled to liquid nitrogen temperatures is utilized. The resulting cryogenically fractured material is then passed through a series of particle size exclusion screens so as to isolate the desired range of particulate acellular tissue matrix material. Once isolated, the particulate acellular tissue matrix material may be freeze-dried so as to remove any moisture that may have been absorbed to the matrix during the above described process.

Figure 1:
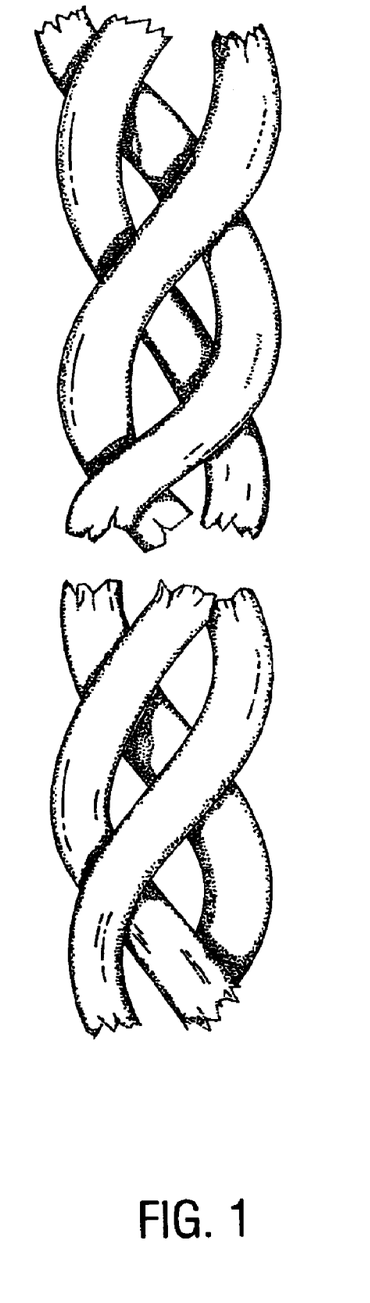
FIG. 1 is an illustration of a bundle of collagen fibers which have been cryofractured in accordance with the present invention.
Figure 2:
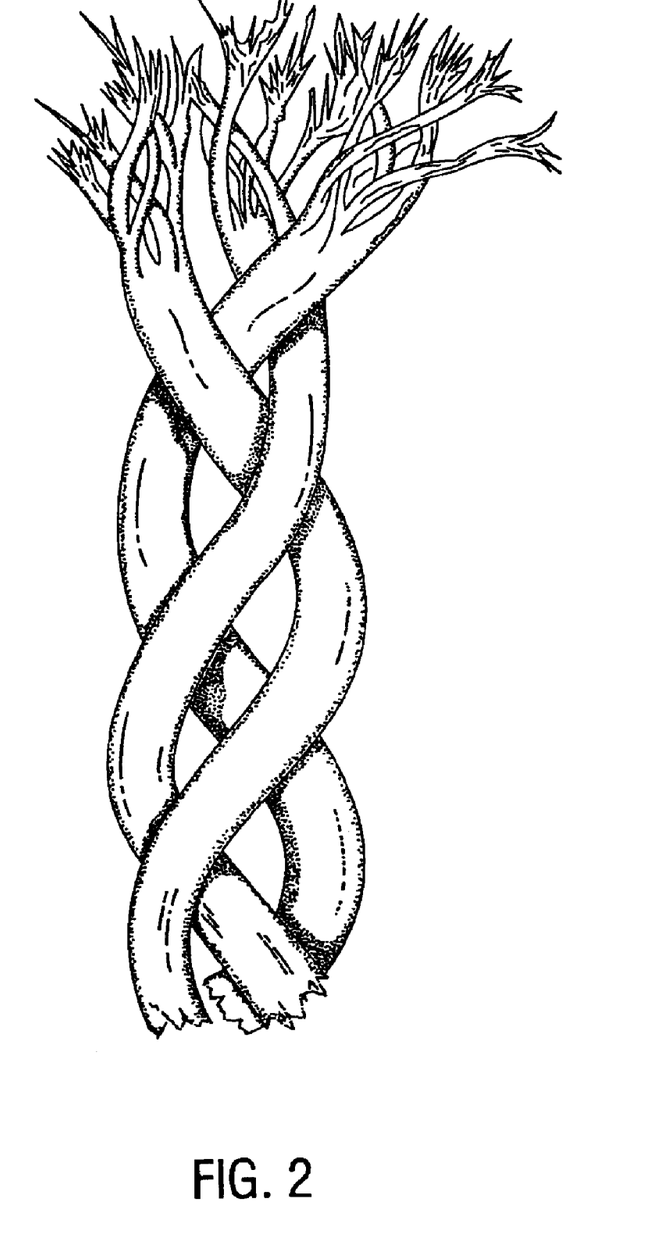
FIG. 2 is an illustration of a bundle of collagen fibers which have been homogenized at room temperature.

Generally the particulate acellular tissue matrix is produced in such a way as to minimize the amount of mechanical damage incurred when reducing an intact tissue to a particulate form. As illustrated in FIG. 1, the cryofracturing of the collagen fibers in accordance with the present invention results in a "clean" break of the collagen fibers. This is in contrast with the frayed ends and substantially damaged collagen fibers that result from the room temperature shredding of collagen tissue as is the practice in the prior art. The damage cause by the mechanical shredding of the collagen fiber bundle, and in particular the end of the collagen fibers is illustrated in FIG. 2. The above illustrations are based on electron microscopic observation of the processed materials and are representative of the ends of the collagen fiber bundles present in the collagen based tissues.

In developing the process of the present invention, several factors were found to be important to the new and unexpected properties of the resulting particulate acellular tissue matrix. One such factor is the temperature at which the homogenization or cryofracturing of the dry acellular matrix, such as AlloDerm®, takes place. As the term is used herein, homogenization and cryofractuing are utilized interchangably and are intended to mean the process of creating particulate material from the sheet like starting material. It has been found that the temperature at which the cryofractuing takes place should be sufficiently enough below room temperature so that the collagen fibers are cryogenically fractured and not shredded or torn. Generally the temperature should be below 0° C. and preferably the temperature should be below about −50° C. and more preferably should be below about −100° C. Commercially available refrigerants can be used to achieve such temperatures, which may include halocarbon refrigerants, liquid carbon dioxide, liquid nitrogen, liquid argon, liquid helium and other similar such well known non-chemically reactive and thus inert and non-toxic refrigerants.

Another factor found to be important in achieving the present invention is the particle size of the particulate acellular tissue matrix material. In order to select the desired range of particles, a cryogenically cooled homogenizing tower is utilized. The role of the homogenization tower is to separate particles which are too small or too large in size from those within the desired particle size range. In one embodiment, liquid nitrogen is utilized in combination with a first metal screen to reject those particles that are too large.

A second metal screen is used in conjunction with liquid nitrogen to capture those particles of the proper minimum size and to allow those particles that are too small to be removed. In one preferred embodiment the first screen is about 0.03 inch (0.0762 cm) metal screen and the second screen is about 0.0015 inch (0.00381 cm) metal screen. In another embodiment the screens are selected so as to isolate particles having a size of about 1 microns to about 900 microns and preferably screens are selected to isolate particles having a size from about 30 microns to about 800 microns.

The resulting particulate acellular tissue matrix may be rehydrated by suspension of the particles in any suitable aqueous solution, preferably normal saline and local anesthetic. If desired the rehydrated particulate acellular tissue matrix may be isolated by filtration or pelletizing the particle via centrifugation and decantation of the supernatant. The particulate acellular tissue matrix may then be resuspended to an appropriate concentration in a suitable physiologically compatible carrier, such as normal saline, normal saline and local anesthetic or if desired a pharmaceutical carrier. Either the physiological carrier or the rehydrating saline solution may contain antibiotics or other drugs, cells or cell extracts, anti-inflammatory agents, proteoglycans, analgesics, hemostatic agents, growth factors such as epidermal growth factor, fibroblast growth factor, nerve growth factor, keratinocyte growth factor, platelet derived growth factor, vasoactive intestinal peptide, stem cell factor, bone morphogenic proteins, chondrocyte growth factor and other similar such components as well as other components that are desirable at the injection site.

Once rehydrated, the particulate acellular tissue matrix may also be combined with stem or progenitor cells prior to or during transplantation into the host. These stem cells may be native to the site of transplantation, but due to their nature need not be. One of ordinary skill in the art should understand and appreciate that upon division, stem cells replicate and also give rise to cells that differentiate further into one or more specialized cells. Such stem cells may include mesenchymal stem cells, epidermal stem cells, cartilage stem cells, hematopoietic stem cells, and other similar cells.

Thus in one illustrative embodiment of the present invention the processing of acellular tissue matrix to create injectable size particles includes: cutting sheets of dry acellular tissue matrix into strips using a modified cutting or meshing devise; homogenization of the dry acellular tissue matrix strips at cryogenic temperatures; separation of the resulting particles by size at cryogenic temperatures; and freeze drying the fraction of particles desired to remove any moisture that may have been absorbed during homogenizing.

Another illustrative embodiment of the present invention includes the processing of acellular tissue derived from a human donor, e.g. AlloDerm®, to create injectable size particles includes: cutting sheets of dry acellular tissue matrix into strips using a modified cutting or meshing devise; equilibration of homogenizing equipment to liquid nitrogen temperatures; addition of dry acellular tissue matrix strips to a liquid nitrogen cooled homogenizer; cryofracturing of the dry acellular tissue matrix strips at liquid nitrogen temperatures; separation of the resulting particles by size at liquid nitrogen temperatures; and freeze drying the fraction of particles desired to remove any moisture that may have been absorbed during homogenizing.

Potential applications of the particulate acellular tissue matrix materials disclosed herein may include: dermatological applications such as acne scar revision, replacement of dermis lost to disease or accident; urological applications such as the relief of incontinence, and vesicoureteral reflux; otolaryngological applications including vocal cord position adjustment; reconstructive surgical applications to replace tissue lost to cancer surgery or other surgical procedures in which there is the removal of tissue; cosmetic surgery procedures such as tissue replacement, reconstruction or augmentation procedures; correctional procedures for gastrointestinal reflux; and other applications which should be appreciated by one of skill in the art. As an illustrative example, see U.S. Pat. No. 5,712,252, the contents of which are hereby incorporated herein by reference and the references cited therein.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a fake or similar result without departing from the scope of the invention.

Preparation Of Acellular Tissue Matrix

The following procedure was carried out in accordance with the teachings of process for producing acellular dermal or other tissue matrix is fully disclosed in U.S. Pat. No. 5,336,616, the entire contents of which is incorporated herein by reference, as well as being the subject of co-pending U.S. Patent Applications including: Ser. No. 09/029,179, filed Aug. 22, 1998, now abandoned; and the contents of which are hereby incorporated herein by reference. This material is commercially available from LifeCell Corporation, The Woodlands Texas.

Donor skin is harvested under aseptic conditions with a dermatome, and maintained at 4° C. in RPMI 1640 tissue culture media containing penicillin and streptomycin solution for no more than 7 days prior to further processing. Transportation to LifeCell's tissue processing center is via overnight delivery, on wet ice, in the same media. On arrival at the processing center, the temperature of the tissue container is verified to be at least 4° C., or the skin discarded. Following verification of container temperature, donor identification and test screening data, the skin is transferred to a laminar-flow hood for further processing.

The donor skin is removed from the transportation container and placed with its reticular side down on a piece of sizing support being a low density polyethylene. An appropriately sized piece of gauze is added to the epidermal side of the skin which is then cut into a rectangular piece as large as possible, not to exceed a 4×4 inch square and no smaller than 2×3 inches. The skin is then placed reticular side down, in a petri dish, to which 50 ml of De-epidermizing Solution consisting of 1 M NaCl is added. The petri dish is then transferred to an incubator and incubated at 37°±2° C. for 18 to 32 hours for human skin and 35 to 55 hours for porcine skin.

After incubation, the petri dish containing the skin is transferred to a laminar flow hood for deepidermization. The gauze is first removed and discarded. The epidermis is then gently grasped with forceps and pulled away from dermis as a sheet. The excess De-epidermizing Solution is then aspirated. A slit approximately one centimeter long is then made in the lower left corner of the dermis to identify the upper and lower surfaces.

The dermis is next rinsed in the same petri dish by the addition of 50 ml Tissue Wash Solution, consisting of sterile Hanks' balanced salt solution. The petri dish is then placed on a rotator at 40±5 RPM for 5 minutes at room temperature (20'-26° C.). The petri dish is then returned to the laminar flow hood and the lid from the petri dish is removed in order to aspirate the Tissue Wash Solution. This procedure is repeated a further two times.

The dermis is then treated with 50 ml. of De-cellularizing solution and the petri dish is placed on a rotator at 40+5 RPM for 1 hour at room temperature (201–26° C.). The decellularizing solution for human skin consists of 0.5% sodium dodecyl sulfate in Hanks' balanced salt solution and for porcine skin contains 1 mM disodium ethylenediamine tetraacetic acid (EDTA). The De-cellularizing solution is removed by aspiration. The dermis is then washed with 50 ml of Tissue Wash Solution. The petri dish is then placed on a rotator at 40+5 RPM for 5 minutes at room temperature (201–26° C.). The Tissue Wash Solution is removed by aspiration. The washing procedure is repeated (2) times. After the dermis has been washed a total of 3 times 50 ml of Pre-freezing Solution is added to the petri dish. The dish is then placed on a rotator at 40+5 RPM for 30 minutes at room temperature (20°–26° C.). The prefreezing solution for human skin consists of 7% dextran (70,000 MWT), 6% sucrose, 6% raffinose and 1 mM disodium ethylenediamine tetraacetic acid in Hanks' balanced salt solution. The pre-freezing solution for porcine skin consists of 7.5% dextran (70,000 MWT), 6% sucrose, 7.5% polyvinylpyrrolidone (MWT 40,000), 1.25% raffinose and 1 mM disodium ethylenediamine tetraacetic acid made up in Hanks' balanced salt solution.

A new piece of gauze is then placed on the papillary side of the dermis and the dermis is turned over so that the reticular side faces up. The backing from the reticular side of the piece of dermis is discarded into a biohazard waste container. An approximately 0.5 to 1.0 cm wide strip of backing and dermis is then cut from the original sample. This strip is then cut into two satellite pieces, each approximately 1.0 cm long. All necessary quality assurance is ultimately performed on these satellite samples, including microbiology and structural analysis.

The tissues are then transferred into individual TYVEK bags. The tissues are positioned in the bag backing side up with the white vent side down. The TYVEK bag is then heat sealed.

The sealed Freeze-dry Bag is transferred to a freeze-dryer which has a minimum shelf temperature of −70° C. and a minimum condenser temperature of −85° C. The tissue is then frozen on the freeze-dryer shelf by ramping the shelf temperature at a rate of −2.5° C./minute to −35° C., and held for at least 10 minutes.

The drying cycle is such that the final residual moisture content of the sample is less than 6% and optimally 2%. In this example, the frozen dermis is dried by the following program:

1. The shelf temperature is ramped at a rate of −2.5° C./minute to −35° C., and held for 10 minutes, with vacuum set to 200 mT (266 Pa).

2. The shelf temperature is then ramped at a rate of 1.5° C./minute to −23° C., and held for 36 hours with vacuum set to 200 mT (266 Pa).

3. The temperature is then ramped at rate of 1.5° C./minute to a shelf temperature of −15° C., and held for 180 minutes with vacuum set to 200 mT (266 Pa).

4. The temperature is then ramped at a rate of 1.5° C./minute to a shelf temperature of −5° C. and held for 180 minutes with vacuum set to 200 mT (266 Pa).

5. The temperature is finally ramped at a rate of 1.5° C./minute to a shelf temperature of 20° C. and held for 180 minutes with the vacuum set to 0 mT (0 Pa).

Following drying, the Freeze-dry Bag containing the dried dermis is unloaded under an atmosphere of dry nitrogen gas, placed in a second predried impervious pouch and heat sealed under the same inert environment.

During the processing procedure and prior to sealing for freeze drying, a satellite sample is cut from the main sample and further processed under identical conditions to the main sample. Prior to use of the main sample in transplantation, all necessary quality assurance is performed on the satellite sample, including microbiology and structural analysis.

Following drying, the sample is stored at above freezing temperatures, optimally 4° C. in a light protected environment.

Preparation Of Particulate Acellular Tissue Matrix

The following procedure utilizes AlloDerm®, an acellular tissue matrix packaged without a backing material the preparation of which is described above. AlloDerm® is commercially available from LifeCell Corporation, The Woodlands Texas. After removal from the packaging, the dry, acellular tissue matrix is cut into strips using a Zimmer mesher fitted with a non-interrupting "continuous" cutting wheel. The resulting long strips of acellular tissue matrix are cut into lengths of about 1 to about 2 centimeters in length.

A homogenizer and sterilized homogenizer probe, such as a LabTeck Macro homogenizer available from OMNI International, Warrenton Va., is assembled and cooled to cryogenic temperatures using sterile liquid nitrogen which is poured into the homogenizer tower. Once the homogenizer has reached cryogenic temperatures, acellular tissue matrix previously prepared into strips as noted above are added to the homogenizing tower containing sterile liquid nitrogen. The homogenizer is then activated so as to cryogenically fracture the strips of acellular tissue matrix. The time and duration of the cryogenic fractionation step will depend upon the homogenizer utilized, the size of the homogenizing chamber, the speed and time at which the homogenizer is operated and should be able to be determined by one of skill in the art by simple variation of the parameters to achieve the desired results.

The cryofractured particulate acellular tissue matrix material is sorted by particle size by washing the product of the homogenizer with liquid nitrogen through a series of metal screens, that have also been cooled to liquid nitrogen temperatures. We have found it especially useful to utilize a combination of screens within the homogenizing tower of the type described above in which the particles are washed and sorted first to exclude oversized particles and then to exclude undersized particles.

Once isolated, the particulate acellular tissue matrix is removed and placed in a vial for freeze drying once the sterile liquid nitrogen has evaporated. This last step is to ensure that any residual moisture that may have been absorbed during the above procedure is removed.

The final product is a white powder having a particle size of about 1 micron to about 900 microns and preferably a particle size of about 30 microns to about 750 microns. Preferably the particles are distributed about a mean of about 150–300 microns. The material is readily rehydrated by suspension in normal saline or other similar suitable rehydrating agent. The rehydrated acellular tissue matrix may be resuspended in normal saline or any other suitable pharmaceutically compatible carrier.

Injection Of Particulate Acellular Tissue Matrix: A sample of the dry cryofractured particulate acellular tissue matrix made in accordance with the procedure disclosed hereinabove was rehydrated and resuspended in phosphate buffer saline at a concentration of about 50 mg of particulate material per milliliter of phosphate buffered saline. The suspension was drawn into 1 cc tuberculin syringes. The samples were sent by overnight delivery at 4° C. to an independent laboratory for injection into test animals. The samples were injected either into the dorsum of the back in the subcutaneous plane or subauricularly (on the back of the ears) of rats. The animals were monitored for 3 days, at which time samples of the skin surrounding and including the area of injection were excised for evaluation. Histological evaluation revealed particles of human dermis just above the subcutaneous muscle layer in the rat. Microscopic examination of the excised tissue revealed that the particulate acellular tissue matrix had been repopulated with rat cells with no evidence of severe acute inflammatory response by the host animal.

Comparison Of Wet Processed And Cryofractured Acellular Tissue Matrix: Samples of both the wet processed (room temperature) particulate acellular tissue matrix and the cryofractured (liquid nitrogen temperature) particulate acellular tissue matrix were prepared in the following manner: Wet processed particulate acellular tissue matrix was made by first rehydrating a sample of AlloDerm® and cutting the rehydrated acellular tissue matrix into strips and homogenizing those strips in phosphate buffered saline at room temperature. The cryofractured particulate acellular tissue matrix was prepared in accordance with the process of the present invention as described hereinabove. Prior to use, the cryofractured particulate acellular tissue matrix was rehydrated in phosphate buffered saline and pelleted using centrifugation.

Samples of each of the resulting particulate acellular tissue matrix materials were suspended in phosphate buffer saline at a concentration of about 50 mg of particulate material per milliliter of phosphate buffered saline. The suspension was drawn into 1 cc tuberculin syringes. The samples were sent by overnight delivery at 4° C. to an independent laboratory for injection into test animals. Samples were injected either into the dorsum of the back in the subcutaneous plane or subauricularly into rats. The animals were monitored for 3 weeks after which samples of the tissue surrounding and including the point of injection were excised for evaluation. Macroscopic and microscopic inspection of the samples revealed the following:

|  | Wet Processed | Cryofractured |
|---|---|---|
| Macroscopic | 1/15* | 12/15* |
| Microscopic | 6/30* | 24/30* |

*# of samples exhibiting persistence of particulate AlloDerm ®/Total # of samples Upon review of the above, one of skill in the art should understand and appreciate that the samples that were processed in accordance with the present invention had a rate of persistence approximately four times that of the wet processed material. From this, such a person should conclude that the wet processed particulate acellular tissue matrix causes fundamental changes to the physiological properties of the acellular tissue matrix resulting in a more rapid degradation or resorption of the sample by the host animal.

Long Term Animal Study: Cryofractured particulate acelluar porcine tissue matrix prepared in accordance with the process of the present invention was injected subcutaneously and subdermally in a pig model organism. A concentration of 150 mg of particulate matrix per milliliter of saline was used in this study. Biopsies from the injection sites were obtained at one, three and six months post-injection. These biopsies revealed evidence of persistence of the particulate matrix at 6 months with no evidence of acute inflammation. Further, the particulate matrix had become repopulated with porcine fibroblasts and exhibited evidence of revascularization of the particulate matrix.

In view of the above disclosure, one of ordinary skill in the art should appreciate that one illustrative embodiment of the present invention includes a method of processing an acellular tissue matrix to give a particulate acellular tissue matrix, the method including: cryofracturing the dry acellular tissue matrix strips at cryogenic temperatures; and separating the resulting particles by size at cryogenic temperatures so as to produce the particulate acellular tissue matrix.

Another illustrative embodiment of the present invention includes a method of processing an acellular tissue matrix to give a particulate acellular tissue matrix. The illustrative the method includes: cryofracturing the dry acellular tissue matrix strips at cryogenic temperatures; separating the resulting particles by size at cryogenic temperatures; and freeze drying the fraction of particles of desired size to remove any moisture that may have been absorbed so as to produce the particulate acellular tissue matrix.

Yet another illustrative embodiment of the present invention included a method of processing an acellular tissue matrix to give a particulate acellular tissue matrix, the method comprising: cutting sheets of dry acellular tissue matrix into strips; cryofracturing the dry acellular tissue matrix strips at cryogenic temperatures; separating the resulting particles by size at cryogenic temperatures; freeze drying the fraction of particles desired size to remove any moisture that may have been absorbed to give a dry particulate acellular tissue matrix; and rehydrating the dry particulate acellular tissue matrix.

In addition to the above methods, the present invention is also directed to the product of the processes described herein. In one illustrative embodiment the product includes the product of the process disclosed herein along with growth and stimulating agents selected from epidermal growth factor, fibroblast growth factor, nerve growth factor, keratinocyte growth factor, platelet derived growth factor, vasoactive intestinal peptide, stem cell factor, bone morphogenic proteins, chondrocyte growth factor and combinations thereof. Another embodiment of the present invention includes the product of the present invention combined with stem cells selected from mesenchymal stem cells, epidermal stem cells, cartilage stem cells, hematopoictic stem cells and combinations thereof. The product of the present invention may also further include analgesic drugs or hemostatic drugs or antibiotic drugs or combinations of these.

While the compositions and methods of this invention have been described in terms of preferred embodiments, it should be apparent to those of skill in the art that variations may be applied to the process described herein without departing from the concept and scope of the invention. All such similar substitutes and modifications apparent to those skilled in the art are considered to be within scope and concept of the invention.

What is claimed is:

1. A method of making a particulate tissue matrix, the method comprising:

fracturing an acellular tissue matrix so as to give a particulate tissue matrix, wherein the acellular tissue matrix: (i) is made from a collagen-containing tissue; (II) is acellular and dehydrated; and (iii) comprises a basement membrane to which, subsequent to rehydration, viable endothelial cells or viable epithelial cells attach.

2. A method of processing an acellular tissue matrix to give a particulate acellular tissue matrix, the method including:

cryofracturing a dry acellular tissue matrix at cryogenic temperatures, wherein the dry acellular tissue matrix comprises a basement membrane to which, subsequent to rehydration, viable endothelial cells or viable epithelial cells attach; and separating the resulting particles by size at cryogenic temperatures so as to produce the particulate tissue matrix.

3. A method of processing an acellular tissue matrix to give a particulate acellular tissue matrix, the method comprising:

cryofracturing a dry acellular tissue matrix at cryogenic temperatures, wherein the dry acellular tissue matrix comprises abasement membrane to which, subsequent to rehydration, viable endothelial cells or viable epithelial cells attach;

separating the resulting particles by size at cryogenic temperatures; and freeze drying the fraction of particles of desired size to remove any moisture that may have been absorbed so as to produce the particulate acellular tissue matrix.

4. A method of processing an acellular tissue matrix to give a particulate acellular tissue matrix, the method comprising:

cutting sheets of dry acellular tissue matrix into strips, wherein the dry acellular tissue matrix comprises a basement membrane to which, subsequent to rehydration, viable endothelial cells or viable epithelial cells attach;

cryofracturing the dry acellular tissue matrix strips at cryogenic temperatures;

separating the resulting particles by size at cryogenic temperatures;

freeze drying the fraction of particles of desired size to remove any moisture that may have been absorbed to give a dry particulate acellular tissue matrix; and rehydrating the dry particulate acellular tissue matrix.

5. The product of the method described in claim 1, 2, 3 or 4.

6. The product of claim 5 further comprising growth and stimulating agents selected from the group consisting of: (a) epidermal growth factor, (b) fibroblast growth factor, (c) nerve growth factor, (d) keratinocyte growth factor, (e) platelet derived growth factor, (f) vasoactive intestinal peptide, (g) stem cell factor, (h) bone morphogenic proteins, (i) chondrocyte growth factor, and (j) combinations of (a)–(i).

7. The product of claim 5 further comprising stem cells selected from the group consisting of (a) mesenchymal stem cells, (b) epidermal stem cells, (c) cartilage stem cells, (d) hematopoietic stem cells, and (e) combinations of (a)–(d).

8. The product of claim 5 further comprising analgesic drugs.

9. The product of claim 5 further comprising hemostatic drugs.

10. The product of claim 5 further comprising antibiotic drugs.

11. The product of claim 5 wherein the dry particulate acellular tissue matrix has a particle size of about 1 micron to about 900 microns.

12. The method described in claim 1, 2, 3 or 4 further comprising applying said particulate acellular tissue to a site in a recipient, said method of applying being selected from the group consisting of (a) injecting, (b) spraying, (c) layering, (d) packing, (e) in-casing and (f) combinations of (a)–(e).

13. The product of claim 11 wherein the dry particulate acellular tissue matrix has a particle size of about 30 microns to about 800 microns.

14. The product of claim 5 wherein the acellular tissue matrix is made from dermis.

15. The product of claim 5 wherein the acellular tissue matrix is made from a tissue selected from the group consisting of blood vessel tissue, heart valve tissue, fascia, and nerve connective tissue.

16. The method of claim 12 wherein said recipient has a defect selected from the group consisting of an acne scar, urinary incontinence, vesicoureteral incontinence, lost tissue, and gastrointestinal reflux.

17. The method of claim 16 wherein the lost tissue is dermis.

18. The method of claim 16 wherein the lost tissue is tissue lost in surgery in which tissue is removed.

19. The method of claim 1, 2, 3 or 4 wherein the acellular tissue matrix is made from a human tissue.

20. The method of claim 1, 2, 3 or 4, wherein the acellular tissue matrix is made from dermis.

21. The method of claim 1, 2, 3 or 4, wherein the acellular tissue matrix is made from a tissue selected from the group consisting of blood vessel tissue, heart valve tissue, fascia, and nerve connective tissue.

* * * * *

UNITED STATES PATENT AND TRADEMARK OFFICE
CERTIFICATE OF CORRECTION

PATENT NO. : 6,933,326 B1
DATED : August 23, 2005
INVENTOR(S) : Stephen A. Livesey et al.

It is certified that error appears in the above-identified patent and that said Letters Patent is hereby corrected as shown below:

Title page,
Item [56], References Cited, U.S. PATENT DOCUMENTS,
"5,800,537" reference, replace "9/1998" with -- 1/1998 --.
FOREIGN PATENT DOCUMENTS, delete the second occurrence of
"CA    1336812    8/1995    A61K/38/39".
OTHER PUBLICATIONS, delete
"*Freeze-Thaw Damage of Saccharomyces-Cerevisiae in Aqueous Cell Suspensions,*" by
K. Hayakawa, Hakkokogaku Kaishi 63(1), 1985, 17-22".

Column 11,
Line 2, replace "(II)" with -- (ii) --.
Line 23, replace "abasement" with -- a basement --.

Signed and Sealed this

Twenty-third Day of May, 2006

JON W. DUDAS
*Director of the United States Patent and Trademark Office*